United States Patent [19]

Adalsteinsson

[11] Patent Number: 4,524,150

[45] Date of Patent: Jun. 18, 1985

[54] STABILIZED MIXTURES OF CARBAMATE INSECTICIDES AND SYNTHETIC PYRETHROIDS

[75] Inventor: Orn Adalsteinsson, Wilmington, Del.

[73] Assignee: E. I. Du Pont de Nemours and Company, Wilmington, Del.

[21] Appl. No.: 469,898

[22] Filed: Mar. 3, 1983

Related U.S. Application Data

[63] Continuation-in-part of Ser. No. 367,754, Apr. 12, 1982, abandoned.

[51] Int. Cl.$^3$ .................. A01N 43/08; A01N 37/34; A01N 47/10; A01N 43/40
[52] U.S. Cl. .................. 514/469; 514/345; 514/351; 514/521; 514/531; 514/534; 514/536; 514/549; 514/550; 514/551; 514/970
[58] Field of Search .............. 424/300, 604, 263, 312, 424/314, 285

[56] References Cited

U.S. PATENT DOCUMENTS

| | | | |
|---|---|---|---|
| 3,035,969 | 5/1962 | Hartle et al. | 167/24 |
| 3,134,712 | 5/1964 | Bywater et al. | 167/30 |
| 3,560,613 | 2/1971 | Miskus et al. | 424/174 |
| 4,299,843 | 11/1981 | Tieman et al. | 424/304 |
| 4,357,348 | 11/1982 | Kasamatsu et al. | 424/300 |

OTHER PUBLICATIONS

The Merck Index 9th ed.–item 5854 (1976), Merck & Co.–Rahway, N.J.
Pesticide Chemical News Guide–Jun. 1, 1981, p. 108.4.
Chemical Abstract 78, 93632(F), (1973)–Eckfeldt.

*Primary Examiner*—Douglas W. Robinson

[57] ABSTRACT

Pesticidal mixtures of carbamate insecticides and synthetic pyrethroids can be improved by the addition of stabilizers to prevent racemization of the pyrethroid to a less pesticidally-active isomeric form.

18 Claims, No Drawings

4,524,150

STABILIZED MIXTURES OF CARBAMATE INSECTICIDES AND SYNTHETIC PYRETHROIDS

RELATED APPLICATION

This application is a continuation-in-part of my copending application U.S. Ser. No. 367,754, filed Apr. 12, 1982 now abandoned.

BACKGROUND OF THE INVENTION

This invention relates to pesticidal mixtures of carbamate compounds and synthetic pyrethroids, and more particularly to improving such mixtures by the addition of certain stabilizers to prevent the racemization of the pyrethroid to a less pesticidally-active form.

Carbamate compounds and synthetic pyrethroids are well known for their control of agricultural pests such as insects and acarids. Although these pesticides are active by themselves, their activities are often selective, being higher against some agricultural pests than against others. Accordingly, various carbamate compounds, such as methomyl, and synthetic pyrethroids have been formulated together, providing mixtures that are more advantageously active against a broader spectrum of pests. Such mixtures are shown, for example, in German Patent DT No. 2805050, published Aug. 10, 1978.

Synthetic pyrethroids usually have one or more asymmetric carbon atoms and consequently exist in two or more stereoisomeric forms. It is well known that not all stereoisomers of a particular pyrethroid possess the same degree of pesticidal activity; usually, a specific isomer or diastereomer pair are more active than is a racemic mixture of all the isomers.

It has been found, however, that some of the synthetic pyrethroids, when resolved or partially resolved to their more pesticidally active isomers, can undergo racemization under certain conditions, reverting back to a less active form. The racemization of one well-known synthetic pyrethroid, deltamethrin, is described in *J. Ag. Food Chem.*, Volume 25, page 1385 (1977). Racemization of pyrethroids, particularly deltamethrin, occurs frequently when they are formulated with carbamate compounds, possibly being caused or accelerated by impurities in the carbamate. The overall pesticidal activity of the mixture is thereby unacceptably reduced, negating the benefits that could otherwise be obtained by combining the two pesticides. Accordingly, an improved mixture in which the broad activity of the mixture is retained would be desirable.

SUMMARY OF THE INVENTION

The present invention provides an improved pesticidal mixture of a carbamate insecticide and a resolved or partially resolved synthetic pyrethroid of the formula:

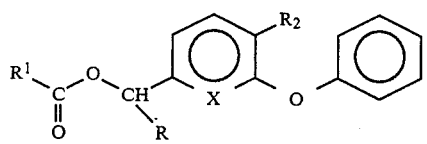

where
R is H or cyano;
$R^1$ is an optionally substituted alkyl cyclopropyl, alkenyl cyclopropyl, or arylalkyl;
$R^2$ is H or F; and
X is C or N;
wherein the improvement comprises the addition of 1-20% by weight, based on the weight of the carbamate, of a stabilizer selected from the group consisting of (a) anhydrides of the formula:

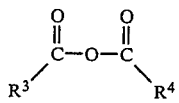

where $R^3$ and $R^4$ independently are $C_1$-$C_4$ alkyl, phenyl, or phenyl substituted with at least one of halogen, lower alkyl, lower alkoxy, or nitro, or $R^3$ and $R^4$ taken together are $C_2$-$C_5$ alkyl, $C_2$-$C_4$ alkenyl,

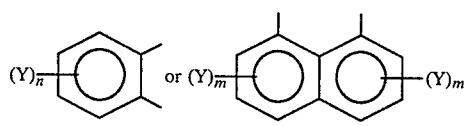

where Y is halogen, lower alkyl, lower alkoxy, or nitro, n is 0-2 and m is 0-1;
(b) isocyanates of the formula $R^5$—N=C=O where $R^5$ is $C_1$-$C_5$ alkyl, or

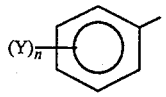

where Y is halogen, lower alkyl, lower alkoxy, or nitro, and n is 0-2;
(c) formaldehyde;
(d) ninhydrin;
(e) fluorescamine; or
(f) mesityl oxide.

DETAILED DESCRIPTION OF THE INVENTION

The present invention is based in part on the discovery that certain compounds will surprisingly act as stabilizers in a mixture of a carbamate insecticide with one or more pesticidal synthetic pyrethroids and will prevent or substantially retard the racemization of the resolved or partially resolved pyrethroids that often occurs when they are combined with carbamate compounds. It is speculated that impurities in the carbamates, inherent in their production or formed during storage, often cause the more pesticidally-active isomer or diastereomer pair of many pyrethroids to racemize to a less active form.

The pyrethroids to which the present invention pertains have at least one asymmetric carbon atom and have the general formula:

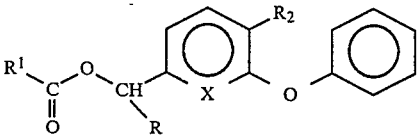

where
R is H or C≡N;
R¹ is an optionally substituted alkyl cyclopropyl, alkenyl cyclopropyl, or arylalkyl;
R² is H or F; and
X is C or N.

When R¹ represents an optionally substituted alkyl cyclopropyl or alkenyl cyclopropyl, preferred compounds are those in which R¹ is:

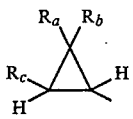

wherein (1) $R_a$ and $R_b$ each represent hydrogen or an alkyl group of 1–6 carbon atoms which may be substituted with up to 3 halogen atoms, preferably F, Cl, or Br, and (2) $R_c$ represents an alkyl group of 1–6 carbon atoms, which may be substituted with up to 4 halogen atoms, or an alkenyl group of 2–6 carbon atoms which also may be substituted with up to 4 carbon atoms. Most preferred of this group of compounds are those wherein $R_a$ and $R_b$ are methyl and $R_c$ is 2,2-dihalovinyl where the halogen atoms are Cl or Br.

When R¹ represents an optionally substituted arylalkyl group, preferred compounds are those in which R¹ is

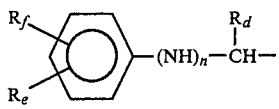

wherein $R_d$ is an alkyl group of 1–6 carbon atoms, n is 0 or 1, $R_e$ is H or a halogen atom, and $R_f$ is a halogen atom, or an alkyl group or an alkoxy group of 1–4 carbon atoms, either of which may be substituted with up to 4 halogen atoms. Most preferred of this group of compounds are those wherein $R_d$ is a branched-chain alkyl group of 3–4 carbon atoms, n is 0, $R_e$ is H, and $R_f$ is F or Cl.

It has been found, for example, that the pyrethroid deltamethrin, available in a fully resolved form, racemizes in the presence of the carbamate methomyl to another isomeric form, R-becythrine, which has about one sixth the pesticidal activity of deltamethrin. Deltamethrin is (S)-α-cyano-3-phenoxybenzyl(1R)-cis-3-(2,2-dibromovinyl)-2,2-dimethylcyclopropanecarboxylate. R-becythrine is (R)-α-cyano-3-phenoxybenzyl-(1R)-cis-3-(2,2-dibromovinyl)-2,2-dimethylcyclopropanecarboxylate. In addition to deltamethrin, other specific examples of synthetic pyrethroids to which the present invention pertains are the pesticidally active isomers, in resolved or partially resolved form, of:

(RS)-α-cyano-3-phenoxybenzyl-(1RS)-cis,trans-3-(2,2-dichlorovinyl)-2,2-dimethylcyclopropanecarboxylate(cypermethrin);

3-(phenoxyphenyl)methyl(±)-cis,trans-3-(2,2-dichlorovinyl)-2,2-dimethyl cyclopropanecarboxylate(permethrin);

(RS)-α-cyano-3-phenoxybenzyl-(RS)-2-(4-chlorophenyl)-3-methylbutyrate(fenvalerate);

(RS)-α-cyano-3-phenoxybenzyl-(RS)-2-(4difluoromethoxyphenyl)-3-methylbutyrate;

cyano-(4-fluoro-3-phenoxybenzyl)-methyl-3-(2,2-dichlorovinyl)-2,2-dimethylcyclopropanecarboxylate;

N-(2-chloro-4-(trifluoromethyl)phenyl)-DL-valine(±)-cyano (3-phenoxyphenyl)methyl ester;

2-(2,2-dichlorovinyl)-3,3-dimethylcyclopropanecarboxylic acid, ester with α-hydroxy-6-phenoxy-2-pyridine acetonitrile;

2-(1,2-dibromo-2,2-dichloroethyl)-3,3-dimethylcyclopropanecarboxylic acid, ester with α-hydroxy-3-phenoxy-benzeneacetonitrile.

The carbamate insecticides that form a part of the improved mixture of this invention are any of those advantageously used to control agricultural pests. Examples are:

aldicarb—2-methyl-2-(methylthio)propionaldehyde O-methylcarbamoyloxime aminocarb—4-dimethylamino-3-methylphenyl methylcarbamate bendiocarb—2,2-dimethyl-1,3-benzodioxol-4-yl methylcarbamate BPMC—2-(1-methylpropyl)phenyl methylcarbamate carbaryl—1-naphthyl methylcarbamate carbofuran—2,3-dihydro-2,2-dimethyl-7-benzofuranyl methylcarbamate carbosulfan—N-((dibutylamino)thio)-2,3-dihydro-2,2-dimethyl-7-benzofuranyl methylcarbamate dioxacarb—ortho-1,3-dioxolan-2-ylphenyl methylcarbamate ethiofencarb—α-(ethylthio)-ortho-tolyl methylcarbamate methomyl—N-(((methylamino)carbonyl)oxy)ethanimidothioate isoprocarb oxamyl—2-(1-methylethyl)phenyl methylcarbamate methyl 2-(dimethylamino)-N-(((methylamino)carbonyl)oxy-2-oxoethanimidothioate promecarb—3-methyl-5-(1-methylethyl)phenyl methylcarbamate propoxur—2-(1-methylethoxy)phenyl methylcarbamate thiodicarb—N,N'-thiobis(N-(((methylamino)carbonyl)oxy)ethanimidothioate)

thiofanox—3,3-dimethyl-1-(methylthio)-2-butanone O-((methylamino)carbonyl)oxime

MPMC—3-methylphenyl methylcarbamate

MTMC—3,4-dimethylphenyl methylcarbamate

Preferred among the carbamate insecticides are methomyl, carbofuran, oxamyl and carbaryl. Methomyl is most preferred.

Mixtures of carbamate insecticides with the above described pyrethroids are improved, according to the present invention, by the addition of from 1–20% by weight, based on the weight of the carbam-ate, of the following stabilizers:

(a) Anhydrides of the formula:

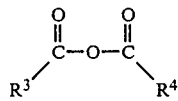

where R³ and R⁴ independently are $C_1$–$C_4$ alkyl or phenyl, or R³ and R⁴ taken together are $C_2$–$C_5$ alkyl, $C_2$–$C_4$ alkenyl,

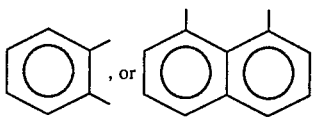

The aromatic anhydrides can be substituted with up to two of halogen, lower alkyl, lower alkoxy, or nitro. Acetic anhydride, glutaric anhydride, benzoic anhydride, and phthalic anhydride are preferred.

(b) Isocyanates of the formula $R^5-N=C=O$ where $R^5$ is $C_1-C_5$ alkyl, or phenyl, optionally substituted with up to two of halogen, lower alkyl, lower alkoxy, or nitro. Phenyl isocyanate is preferred among the isocyanates.

(c) Formaldehyde.

(d) Ninhydrin, which can be in the hydrated form, having the structure

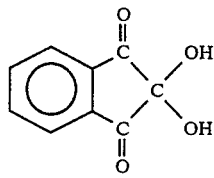

or in the anhydrous form, having the structure

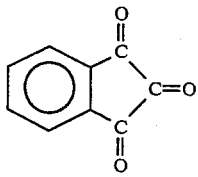

(e) Fluorescamine, which has the formula

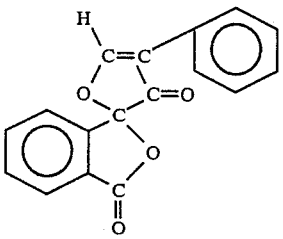

and can be prepared as described in U.S. Pat. No. 3,957,826, issued May 18, 1976 to Leimgruber, et al.

(f) mesityl oxide.

Of the above stabilizers, most preferred are benzoic anhydride and phthalic anhydride for their effectiveness and ease of formulation, and fluorescamine for its effectiveness.

The improvements of this invention, the prevention or retardation of the racemization of the pyrethroid, are evident when as little as 1% by weight, based on the weight of the carbamate, of at least one of the above stabilizers is added to the mixture. Preferred ranges are 4-16% by weight, based on carbamate weight, of the stabilizer. It is to be understood that combinations of two or more of the above stabilizers can also be used, and in such case, the above weight percentages refer to the total of all stabilizers used in the mixture.

The amount of stabilizer used within the above stated ranges can vary also with the manner by which the carbamate is made. This is particularly true in the case of methomyl. Generally, compositions using methomyl made by a process in which it is crystallized out of a solution, such as is shown in U.S. Pat. No. 3,576,834, will require relatively less stabilizer than will compositions using methomyl made by a solvent-free process, such as that shown in U.S. Pat. No. 3,855,620. For example, when benzoic anhydride or phthalic anhydride, two preferred stabilizers, are formulated with methomyl made by crystallization, the anhydride is present at a concentration of about 7-11% by weight, based on the methomyl weight.

Since, as discussed, the amount of stabilizer to be used can vary with the manner by which the carbamate insecticide is made, the length of its storage period, and with the identity of the stabilizer, those skilled in the art will recognize that an amount that will be effective to substantially prevent racemization can not be stated with precision. Generally, however, the use of the above stated ranges will lead to desirable results.

Overall, preferred mixtures of this invention are mixtures of methomyl and deltamethrin that are improved with the addition of 4-16% by weight, based on methomyl weight, of benzoic anhydride, phthalic anhydride, or fluorescamine. Most preferred of these is benzoic anhydride.

The pesticidal mixtures to which the present invention applies are those having a carbamate/pyrethroid weight ratio 0.05-100, preferably 1-50, and most preferably 2-30. The improved mixtures can be dissolved or dispersed in various liquid diluents such as water, ketones, alcohols, or aromatic solvents. Cyclohexanone, methanol, and xylene are preferred organic liquids for this purpose. It should also be noted that when the stabilizer is an isocyanate, the use of water as a diluent should be avoided since its presence can diminish the stabilizing effect of the isocyanate.

When the improved pesticidal mixtures are dispersed in such organic liquids, it is often desirable to use a surfactant to maintain the dispersion. Examples of surfactants that can be used are blends of oil-soluble sulfonates with polyoxyethylene ethers, aromatic sulfonate-oxides, sorbitan monolaurates, alkyl aryl polyether alcohols, such as octylphenoxypolyethoxy ethanol (sold as Triton X-100), and the amine salts of dodecyl benzenesulfonic acid.

Useful formulations of the improved carbamate/pyrethroid mixtures can be prepared in conventional ways. These include granules, wettable powders, emulsifiable concentrates and the like. Many of these can be applied directly to the locus of the plants to be protected from agricultural pests. Sprayable formulations, for example, can be used in the compositions as indicated below or can be extended in a suitable medium and used at spray volumes of from about 0.5-150 liters per acre. The formulations, as mentioned, will contain active ingredients (carbamate and pyrethroid), stabilizers, and optionally solid or liquid diluents and surfactants, in the following weight proportions:

| | Parts by Weight | | |
|---|---|---|---|
| | Wettable Powders | Oil Suspensions, Emulsions, Solutions (including Emulsifiable Concentrates) | Granules |
| Active Ingredient(s) | 10–90 | 5–50 | 1–95 |
| Diluent(s) | 0–90 | 40–95 | 5–99 |
| Surfactant(s) | 1–10 | 0–15 | 0–15 |
| Stabilizer(s) | 0.1–15 | 0.05–10 | 0.01–15 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders. Typical liquid diluents and solvents are described in Marsden, "Solvents Guide," 2nd Ed., Interscience, New York, 1950 and in "McCutcheon's Detergents and Emulsifiers Annual", McCutcheon's Division of the Manufacturing Confectioner Publishing Co., Glen Rock, N.Y. Sisely and Wood, "Encyclopedia of Surface Active Agents", Chemical Publishing Co., Inc., New York, 1964, list surfactants and recommended uses. All formulations can contain minor amounts of additives to reduce foaming, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Granules can be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, New York, 1963, pp. 8–59ff.

In the following examples, all methomyl was produced by a process in which it was crystallized out of a solution, such as is shown in U.S. Pat. No. 3,576,834.

EXAMPLES 1–10

Simple mixtures of methomyl, deltamethrin, solvent, and (except Example 5) stabilizer were prepared. The mixtures were aged, in closed containers, for 3 weeks at a temperature of 45° C., conditions designed to simulate shelf-storage over a period of at least one year. At the end of the 3-week period, the mixtures were analyzed by high pressure liquid chromatography to determine whether any conversion to R-becythrine, which was not present in the initial mixture, had occurred. All weights are expressed as a percentage of the total mixture weight.

| Example | 1 | 2 | 3 | 4 | 5 |
|---|---|---|---|---|---|
| Methomyl | 25.0 | 20.0 | 26.0 | 25.0 | 25.5 |
| Deltamethrin | 2.0 | 2.0 | 2.0 | 2.0 | 2.0 |
| Cyclohexanone | 71.0 | 77.8 | 70.0 | 71.0 | 72.5 |
| Acetic anhydride | 2.0 | — | — | — | — |
| Fluorescamine | — | 0.2 | — | — | — |
| Phenylisocyanate | — | — | 2.0 | — | — |
| Formaldehyde | — | — | — | 2.0 | — |
| | 100.0 | 100.0 | 100.0 | 100.0 | 100.0 |
| R-becythrine after 3 weeks at 45° C. | 0.0 | 0.0 | 0.1 | 0.1 | 0.4 |

| Example | 6 | 7 | 8 | 9 | 10 |
|---|---|---|---|---|---|
| Methomyl | 25.0 | 25.0 | 25.0 | 25.0 | 25.0 |
| Deltamethrin | 2.0 | 2.0 | 2.0 | 2.0 | 2.0 |
| Emulsifiers | 4.0 | 4.0 | 4.0 | 4.0 | 4.0 |
| Solvents (xylene cyclohexanone, water, methanol) | 65.0 | 65.0 | 65.0 | 65.0 | 65.0 |
| Benzoic anhydride | 4.0 | — | — | — | — |
| Butyric anhydride | — | 4.0 | — | — | — |
| Mesityl oxide | — | — | 4.0 | — | — |
| Maleic anhydride | — | — | — | 4.0 | — |
| Naphthalic anhydride | — | — | — | — | 4.0 |
| | 100.0 | 100.0 | 100.0 | 100.0 | 100.0 |
| R-becythrine after 3 weeks at 45° C. | 0.0 | 0.11 | 0 | 0.05 | 0.13 |

EXAMPLES 11–13

Mixtures of methomyl, deltamethrin, solvent, surfactant, and stabilizer were prepared, aged, and analyzed in a manner similar to that of Examples 1–5. All weight are expressed as a percentage of the total mixture weight.

| Example | 11 | 12 | 13 |
|---|---|---|---|
| Methomyl solution (25% by weight methomyl in inert liquid diluent) | 88.5 | 88.5 | 88.5 |
| Deltamethrin | 1.7 | 1.7 | 1.7 |
| Solvent (cyclohexanone and xylene) | 5.8 | 5.8 | 5.8 |
| Surfactant (blends of oil-soluble sulfonates with polyoxyethylene ethers) | 1.5 | 1.5 | 1.5 |
| Phthalic anhydride | 2.5 | — | — |
| Ninhydrin | — | 2.5 | — |
| Glutaric anhydride | — | — | 2.5 |
| | 100.0 | 100.0 | 100.0 |
| R-becythrine After 3 weeks at 45° C. | 0.01 | 0.12 | 0.11 |

In control Example 5, 20% of the deltamethrin had racemized to R-becythrine. Illustrating the present invention, in Examples 1, 2, 6 and 8, no racemization was detected; in the remaining Examples, where some racemization occurred, it was limited to a maximum of about 7% (Example 12).

EXAMPLE 14

Mixtures of methomyl, deltamethrin, solvent, surfactant, and stabilizer were prepared, aged, and analyzed in a manner similar to that of the previous examples. All weights are expressed as a percentage of the total mixture weight.

| | |
|---|---|
| Methomyl | 27.6 |
| Deltamethrin | 1.71 |
| Surfactants | 4.0 |
| Phthalic anhydride | 2.0 |
| Solvent | 64.69 |
| | 100.0 |
| R-becythrine After 3 weeks | 0.02 | at 45° C.

What is claimed is:

1. An improved insecticidal mixture of a carbamate insecticide and a resolved or partially resolved synthetic pyrethroid of the formula:

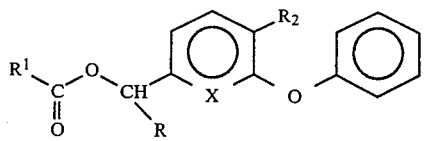

where R is H or cyano; $R^1$ is an optionally substituted alkyl cyclopropyl, alkenyl cyclopropyl, or $R^1$ has the formula:

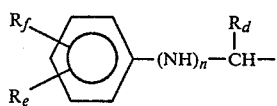

wherein (1) $R_d$ is $C_1$–$C_6$ alkyl, (2) $R_e$ is H or halogen, (3) $R_f$ is halogen, $C_1$–$C_4$ alkyl, $C_1$–$C_4$ haloalkyl having 1–4 halogen atoms, $C_1$–$C_4$ alkoxy, or $C_1$–$C_4$ haloalkoxy having 1–4 halogen atoms, and (4) n is 0 or 1; $R^2$ is H or F; and X is C or N; and where the weight ratio of carbamate to pyrethroid is about 1:1 to 50:1; wherein the improvement comprises the addition of 1–20% by weight, based on the weight of the carbamate, of an anhydride stabilizer of the formula:

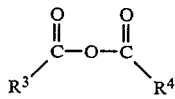

where $R^3$ and $R^4$ independently are $C_1$–$C_4$ alkyl or phenyl, or $R^3$ and $R^4$ taken together are $C_2$–$C_5$ alkyl, $C_2$–$C_4$ alkenyl,

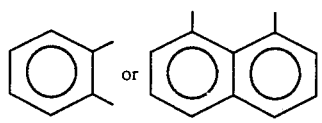

2. An improved mixture of claim 1 wherein R is cyano and the carbamate insecticide is methomyl, oxamyl, carbaryl, or carbofuran.

3. An improved mixture of claim 2 wherein the stabilizer is benzoic anhydride, phthalic anhydride, glutaric anhydride or acetic anhydride.

4. An improved mixture of claim 3 where the stabilizer is benzoic anhydride.

5. An improved mixture of claim 3 or 4 wherein the pyrethroid is deltamethrin and the insecticide is methomyl.

6. An improved mixture of claim 5 wherein there is 4–16% by weight, based on the weight of the methomyl, of the anhydride stabilizer.

7. An insecticidal composition comprising a surfactant, a diluent, or combination thereof, and an insecticidally effective amount of an improved mixture of claim 1.

8. An insecticidal composition comprising a surfactant, a diluent, or combination thereof, and an insecticidally effective amount of an improved mixture of claim 2.

9. An insecticidal composition comprising a surfactant, a diluent, or combination thereof, and an insecticidally effective amount of an improved mixture of claim 3.

10. An insecticidal composition comprising a surfactant, a diluent combination thereof, and an insecticidally effective amount of an improved mixture of claim 4.

11. An insecticidal composition comprising a surfactant, a diluent, or combination thereof, and an insecticidally effective amount of an improved mixture of claim 5.

12. An insecticidal composition comprising a surfactant, a diluent, or combination thereof, and an insecticidally effective amount of an improved mixture of claim 6.

13. A method for control of insects which comprises applying to a locus to be protected an insecticidally effective amount of an improved mixture of claim 1.

14. A method for control of insects which comprises applying to a locus to be protected an insecticidally effective amount of an improved mixture of claim 2.

15. A method for control of insects which comprises applying to a locus to be protected an insecticidally effective amount of an improved mixture of claim 3.

16. A method for control of insects which comprises applying to a locus to be protected an insecticidally effective amount of an improved mixture of claim 4.

17. A method for control of insects which comprises applying to a locus to be protected an insecticidally effective amount of an improved mixture of claim 5.

18. A method for control of insects which comprises applying to a locus to be protected an insecticidally effective amount of an improved mixture of claim 6.

* * * * *